United States Patent [19]

Greco et al.

[11] Patent Number: 4,749,585

[45] Date of Patent: Jun. 7, 1988

[54] ANTIBIOTIC BONDED PROSTHESIS AND PROCESS FOR PRODUCING SAME

[75] Inventors: Ralph S. Greco, Princeton; Richard A. Harvey, East Brunswick; Stanley Z. Trooskin, North Brunswick; George Strauss, Piscataway, all of N.J.

[73] Assignees: University of Medicine and Dentistry of New Jersey, Newark; Rutgers University, New Brunswick, both of N.J.

[21] Appl. No.: 850,848

[22] Filed: Apr. 11, 1986

[51] Int. Cl.$^4$ .............................................. A01N 1/02
[52] U.S. Cl. ................................ 427/2; 128/334 R; 623/1; 623/12; 623/11; 623/66; 521/30
[58] Field of Search ..................... 427/2; 128/334 R; 623/1, 12, 11, 66; 521/30

[56] References Cited

U.S. PATENT DOCUMENTS 4,442,133 4/1984 Greco et al. .......................... 427/2

OTHER PUBLICATIONS

Federation Proceedings: Jan. 1985, p. 226.
Abstracts, Int. Sym. on Artificial Organs, Biomed. Eng. & Transplantation, Jan. 20–23, 1986.

Primary Examiner—John Kight
Assistant Examiner—M. L. Moore
Attorney, Agent, or Firm—David A. Jackson; Richard M. Goldberg; Barbara L. Renda

[57] ABSTRACT

There is disclosed an improved prosthesis coated, respectively, with an ionic surfactant, an antibiotic and/or antithrombiotic agent and treated with an immobilizing ionic exchange compound, to remove un-antibiotic bound ionic surfactant. The drug may be encapsulated within phospholipid vesicles which are bound to the prosthesis.

20 Claims, No Drawings

ANTIBIOTIC BONDED PROSTHESIS AND PROCESS FOR PRODUCING SAME

BACKGROUND OF THE INVENTION

This invention was made with Government support under Grant HL 24252 awarded by the National Institutes of Health. The Government has certain rights in this invention.

FIELD OF THE INVENTION

This invention relates to drug bonded implants, and more particularly relates to improved surgical implants having extended antibiotic activity, reduced thromogenicity and method for producing same.

DESCRIPTION OF THE PRIOR ART

In an abstract presented in November 1979 to the Association for Academic Surgery, there is disclosed the bonding of oxacillin to a polytetrafluoroethylene surface coated with benzalkonium chloride for protection against infection by the device as a result of surgical implantation.

In U.S. Pat. No. 4,442,133 issued Apr. 10, 1984, there is disclosed a process for coating vascular prostheses with a cationic surfactant, such as tridodecylmethyl ammonium chloride to increase sites for antibiotic bonding, and then prior to utilization, the thus coated vascular protheses are placed in an antibiotic solution to bond the antibiotic thereto. Such antibiotic bonded vascular prostheses exhibit resistance to infection.

OBJECTS OF THE INVENTION

An object of the present invention is to provide improved implantable devices having an antibiotic bonded thereto.

Yet another object of the present invention is to provide an improved implantable device having an antibiotic bonded in such a way as to substantially eliminate thrombosis of said implant.

Another object of the present invention is to provide an improved implantable device having an antibiotic bound thereto of improved release times.

SUMMARY OF THE INVENTION

These and other objects of the present invention are achieved by a prosthesis coated, respectively, with an ionic surfactant and an antibiotic, and/or antithrombotic agent. The drug may be encapsulated in phospholipid vesicles which are then bound to the surfactant coated prosthesis.

DEFINITION OF TERMS

The term "prosthesis" employed herein and throughout the present specification and claims is intended to include:
intravenous, peritoneal dialysis, parenteral and urological catheters;
vascular grafts;
ventricular and peritoneovenous shunts;
penile prostheses;
heart valves;
orthopedic prostheses (including hip and knee replacements);
intraocular prostheses (including lenses and cornea);

These device are well known and have been described heretofore for various purposes, including intravenous feeding, peritoneal dialysis, reconstruction of arteries and veins, orthopedic repair, in addition to other uses. These devices will consist of organic polymers and/or metallic materials including:
dacron
nylon
polyacrylamide
polycarbonate
polyethylene
polyformaldehyde
polyglycolic acid
polylactic acid
polymethylmethacrylate
polypropylene
polystyrene
polytetrafluoroethylene
polytrifluorochlorethylene
polyvinylchloride
polyurethane
elastomeric organosilicon polymers, such as polysiloxanes, eg. Silastic ®;
cobalt-chromium alloys
stainless steel
titatium The term "surfactant" as employed herein and throughout the present specification and claims is intended to include cationic and anionic compounds with surface-active properties. These materials are well known and have been described heretofore for various purposes, including wetting, penetrating, emulsifying, dispersing and solubilizing, in addition to other uses.

The anionic surfactants may be divided into the following major classes:
Alkyl aryl sulfonates
Alkyl sulfates
Alkyl sulfonates
Sulfated and sulfonated amines
Sulfated and sulfonated esters and ethers Specific examples from this group of anionic surfactants are the following:
Disodium bis(sulfonaphthyl)-methane
Polyoxyethylene sorbitan monostearate
Sodium bis (tridecyl)-sulfosuccinate
Sodium N-methyl-N-methyl-n-oleoyl taurate
Sodium lauryl sulfate
Sodium octylphenoxy polyglycol sulfonate
Sodium alkylbenzenesulfonate
Sodium isopropylnaphthalenesulfonate
Sodium heptadecyl sulfate
Taurcholic acid The cationic surfactants may be divided in the following major classes:
Quarternary ammonium salts
Salts of simple primary and tertiary amines
Salts and quaternary derivatives of amino acids
Salts and quaternary derivatives of amino esters
Salts and quaternary derivatives of imidazoline Specific examples from this group of cationic surfactants include the following:
Benzalkonium chloride
Dimethyl benzyl cetylammonium chloride
Dimethyl 2-hydroxyethyl stearamidopropylammonium nitrate
Dimethyl benzyl stearamidopropyl ammonium chloride
Tridodecylmethylammonium chloride The term "phospholipid" employed herein and throughout the present specification and claims is intended to include the compounds listed below. These compounds are well known and have been described heretofore for various purposes, including the formation of phospholipid vesicles.

phosphatidic acid
phosphatidylinositol
phosphatidylserine
phosphatidylethanolamine
phosphatidycholine
plasmalogens (ether lipids)

The term "drug" employed herein and throughout the present specification and claims is intended to include those which are listed below. These compounds are well known and have been described heretofore for various purposes, including the intravenous administration for the prevention of infections and thrombus formation.

ANTIBIOTICS aminoglycoside
amphotericin
ampicillin
carbenicillin
cefazolin
cephalosporin
chloroamphenicol
clindamycin
erythromycin
gentamycin
griseofulvin
kanamycin
methicillin
nafcillin
novobiocin
penicillin
polymyxin
refampin
streptomycin
sulfamethoaxozole
sulfonamide
tetracycline
trimethoprim
vancomycin

ANTI-THROMOBOTIC DRUGS INCLUDING acetylsalicylic acid
dipyridamole
heparin
ibuprofen
indomethacin
prostaglandins
sulfinpyrazone
warfarin

THROMBOLYTIC ENZYMES streptokinase
urokinase
plasminogen activator

DETAILED DESCRIPTION OF THE INVENTION

To facilitate an understanding of the present invention, the present invention will be described with reference to the treatment of a vascular prosthesis prepared from thermoplastic substrates, such as polytetrafluoroethylene, dacron, polyethylene, Silastic ® and the like, although it will be understood by one skilled in the art that the present invention relates to the treatment of any implantable device formed from such materials, e.g. catheters, heart valves, orthopedic implants, sutures, profusion pumps, etc.

In accordance with the present invention, grafts of the thermoplastic substrates, such as polytetrafluoroethylene or dacron, are cut into 0.5 cm segments and placed in a solution of a cationic surfactant, such as a 5% ethanol solution of tridodecylmethyl ammonium chloride (TDMAC) for a period of time of from 5 to 120 minutes, preferably about 30 minutes, at a temperature of from 0 degrees to 55 degrees C., preferably at ambient temperature. The grafts are air dried and thoroughly washed in distilled water to remove excess TDMAC.

The grafts having an absorbed coating of TDMAC are then placed in oxacillin, ticarcillin, carbenicillin, the cephalosporins or cefoxitins for a period of time of from 5 to 120 minutes, preferably 60 minutes, at a temperature of from 0 degrees to 35 degrees C., preferably 25 degrees C. The thus treated grafts are then thoroughly washed, preferably in distilled water to remove unbound antibiotic material, it being understood that not all of the unbound antibiotic material is removed from the thus treated grafts.

The grafts having TDMAC/antibiotic compound bound thereto are immersed in a slurry of a particulate immobilizing cation exchange compound, such as Sepharose-CM, cross-linked agarose having carboxymethyl groups ($CH_2$—COO—) attached thereto, for a period of time of from 6 to 72 hours, preferably 20 hours, at a temperature of from 0 degrees to 35 degrees C., preferably 25 degrees C. The immobilizing cation exchange compound is in the form of beads having a particle size distribution of from 40 to 120 microns and is commerically available in such particle size distribution. The thus treated grafts are then thoroughly washed in distilled water.

Implantable devices or prostheses treated in accordance with the present invention improve the molar ratio of antibiotic compound binding per TDMAC molecule of up to 0.5, i.e. one molecule of antibiotic compound to two molecules of cationic surfactant, as compared with the molar ratio of 0.25, i.e. a one-hundred percent (100%) increase, as compared by the process of the hereinabove discussed U.S. Letters Patent, the disclosure of which is incorporated herein by reference.

While Applicant does not wish to be bound by any theory of invention, it appears that the immobilizing cation exchange compound has a high affinity for bound TDMAC molecules which are not shielded by a bound antibiotic molecule, and thus reduce any thrombotic effect exerted by the TDMAC. Further, the surface of the prosthesis, at a microscopic level, if filamentous with ridges and deep recesses. The molecules of TDMAC and antibiotic compound are relatively small and presumably bind uniformly on the exposed ridges and the interstices of the prosthesis surface.

The particles of the immobilizing cation exchange compound, such as Sepharose-CM, is sterically unable to penetrate into the deep valleys and surfaces of the prosthesis. Thus, the TDMAC and antibiotic molecules remain bonded in such recesses for a longer period of time. It has preliminarily been found that the amount of antibiotic compound remaining after exposure to plasma is more slowly released (t ½ = 12 hours) as compared with a prosthesis not treated with an immobilizing cation exchange compound (t ½ = 2 hours). Thus, the present invention yields a surface which is less thrombogenic, yet contains a sequestered reservoir of an antibiotic compound, and exhibits a reduced tendency to cause blood platelet aggregation.

As hereinabove discussed, the beads of immobilizing cationic surfactant (commercially available) are of a particle size distribution of from 40 to 120 microns. It is believed that still further improved results would be obtained if the particle size distribution of the beads were more closely that of the diameter of the blood platelets, i.e. about 2 microns. Thus, the beads of such a size of the cation exchange compound would be permitted to move more closely into the recess of a treated device to remove more of the un-antibiotic bound TDMAC molecules.

In addition to Sepharose-CM, effective cation exchange compounds include Sulphopropylcellulose (SP-Sephadex), etc.

This and other related processes of binding antibiotics directly to the charged surface of a prosthesis are limited by the fact that the rate of dissociation of antibiotic from the prosthesis cannot be controlled, and by the requirement that the antibiotic to be bound must be charged. This restriction may be eliminated by coating the surface of a surfactant-treated prosthesis with phospholipid vesicles (liposomes) containing entrapped antibiotics or anti-thromobotic agents. In this approach, the drugs are first packaged in a liposome containing a net electrical charge prior to binding to the prosthesis. For example, liposomes prepared from phosphatidylserine carry a net negative charge and as described below, tenaciously bind to prostheses treated with TDMAC, a positively charged surfactant. Drug molecules, passively entrapped in the aqueous phase of these liposomes, are retained on the prosthesis due to interaction of the liposome with TDMAC. Significantly, the antibiotic itself need not be negatively charged, permitting the use of electrically neutral or even positively charged drugs. Further, the rate of release of the entrapped antibiotic from the surface of the prosthesis is determined by the stability of the liposome. By varying the composition of the liposome (eg. by adding from 1% to 10% cholesterol to phospholipids), it is possible to tailor the rate of antibiotic release to achieve optimal anti-bacterial effects for any clinical situation.

In practicing the invention, the prosthesis is first coated with a surfactant. A cationic surfactant is employed if negatively charged phospholipid vesicles (containing encapsulated dry molecules) are subsequently to be attached to the surface of the surfactant-treated prosthesis. Conversely, an anionic surfactant is employed if positively charged phospholipid vesicles (containing encapsulated drug molecules) are to be attached to the surface of the surfactant-treated prosthesis. For convenience, the method is described using a cationic surfactant, tridodecylmethylammonium chloride (TDMAC) and commercially available vascular prostheses, 0.5 cm×0.6 cm in diameter, fabricated from polytetrafluoroethylene (PTFE). However, the method is in no way limited to this specific surfactant or prosthesis.

The prosthesis is soaked for from 2 to 600 minutes, but preferably for 5 minutes, in a solution of TDMAC, 0.1% to 50% by weight, but preferably 5% or less, in ethanol. The prosthesis is dried at room temperature in room air and washed in distilled water. Vesicles containing encapsulated drug molecules are prepared by sonicating phospholipids suspended in an aqueous solution of the drug. A phospholipid with a net negative charge is employed if the prosthesis has been coated with positively charged surfactant. Conversely, a phospholipid with a net positive charge is employed if the prosthesis has been coated with negatively charged surfactant. For convenience, the method is described using a phosphotidyl serine, a phospholipid with a net negative charge, capable of binding to a prosthesis coated with a positively charged surfactant, TDMAC.

A solution of 10 mg of phosphatidyl serine in chloroform is dried under vacuum in a rotary evaporator to form a thin film on the wall of a flask. One ml of an aqueous solution containing 2 millimolar Tris buffer at pH 7.5, containing the drug to be encapsulated is added at a final concentration of 0.01 mg/ml to 50 mg/ml, but preferably 10 mg/ml. The mixture is briefly agitated on a vortex mixer to disperse the lipid. The suspension is then sonicated with a probe-type sonicator at 5 watts to 50 watts, but preferably 20 watts of energy, until the suspension is only slightly turbid. This typically requires 60 minutes. A constant temperature water bath is used to maintain the temperature at 25° C. The suspension is finally diluted with 2 millimolar Tris buffer at pH 7.5.

The surfactant-treated prosthesis is incubated with 2 ml of the phospholipid vesicle suspension for 16 hours at room temperature. It is rinsed in water to remove adhering (but not bound) vesicles. The prosthesis is now ready for surgical implantation.

Analysis of the modified prosthesis resulting from the present invention is performed as follows:

Amount of phospholipid vesicles bound: Binding of the phospholipid vesicles to the prosthesis is quantitated by including a small amount (0.05 mg) of a hydrophobic fluorescence dye (dioctadecyl oxacarbocyanine) with the phospholipids prior to the formation of vesicles by sonication. The dye acts as a convenient probe for liposome formation since in aqueous suspension the molecule is non-fluorescent, but has a srong fluorescence emission when intercalated in the lipid bilayer of liposomes. Specifically, the prosthesis which has been coated with liposomes marked with fluorescence is extracted for five minutes in 2 ml of chloroform which destroys the integrity of the vesicle by dissolving the phospholipid and the fluorescent dye. The fluorescence of the chloroform extract, therefore, is a measure of the amount of liposomes bound to the surface of the prosthesis. The resultant suspension was strongly fluorescent indicating the presence of liposomes. Typical results are shown below (for convenience we have arbitrarily designated the fluorescent intensity of the solution as 100 units):

| FRACTION EXAMINED | RELATIVE FLUORESCENCE |
|---|---|
| vesicle suspension before exposure to prosthesis | 100 |
| vesicle suspension after 16 hours exposure to prosthesis | 75 |
| chloroform extract of prosthesis | 22 |

These data show that 2.2%, or 2.18 mg of the negatively charged phosphatidyl serine vesicles bound to the prosthesis coated with positively charged surfactant. Prostheses not treated with TDMAC do not bind phosphatidyl serine vesicles. Vesicles from phosphatidylcholine or phosphatidylcholine and cetylphosphate (which are neutral or only weakly negative) do not bind to the TDMAC-treated prosthesis.

Stability of bound liposome to plasma: The stability of bound liposomes in the presence of human plasma was determined. Liposomes formed form phosphatidylserine were bound to polytetrafluoroethylene as described above. The prostheses were then incubated in plasma for 1 hour at room temperature. Following a water wash, the liposomes were stripped from the polytetrafluoroethylene by treatment with chloroform and the fluorescence determined.

| TREATMENT | FLUORESCENCE |
|---|---|
| Extract from PTFE control not exposed to plasma | 26 |
| Extract from PTFE exposed to plasma | 23 |

These data indicate that the liposomes prepared from phosphatidylserine remain bound to TDMAC-treated polytetrafluoroethylene prosthesis in the prsence of plasma. Prolonged exposure to plasma result in the slow disintegration of surface-bound liposomes resulting in the release of drugs entrapped in the vesicle.

Entrapment of molecules by liposomes: The ability of the liposomes to entrap molecules in aqueous solution was tested using 14 C-labeled glycerol as a solute. 14 C-Glycerol is water-soluble organic compound whose presence can be detected by scintillation counting (see below) and is useful as a model for encapsulated drug molecules. Liposomes were prepared in the usual way except that the Tris buffer contained radiolabelled glycerol, 10 mg/ml. The liposome were bound to polytetrafluoroethylene as described above. The prosthesis was washed three times in water to remove glycerol not entrapped in liposomes. The amount of radioactive glycerol bound was determined by liquid scintillation counting of the entire prosthesis.

Controlled experiments confirmed that free glycerol is not bound to either polytetrafluoroethylene or TDMAC treated polytetrafluoroethylene. From the radioactivity present, it was calculated that 110 $\mu$g of glycerol was bound per cm of polytetrafluoroethylene. This corresponds to entrapment of 11 $\mu$l of aqueous solution per cm of prosthesis.

In actual clinical practice, the contents of the liposomes would be substances other than glycerol, which was employed as a typical low molecular-weight model compound merely to demonstrate the feasibility of the process. For example, in practicing the invention, antibiotic and/or antithrombotic agents would be encapsulated. Over the course of days to weeks the liposomes slowly release from the implanted prosthesis their entrapped drugs creating a local environment which is antibacterial and/or resists the formation of thrombi, depending on the drug employed.

As noted earlier, the present invention may be practiced by application to a variety of substrates, including bio-compatible metals such as those listed earlier herein. The same procedures for the practice of the present invention would control regardless of the particular substrate. Reference in this regard is made to copending Application Ser. No. 852,849, filed concurrently herewith, the disclosure of which is incorporated herein by reference, wherein the binding of surfactant and antibiotic to metallic surfaces is treated in greater detail.

Numerous modifications and variations of the present invention are possible in light of the above teachings and, theretofore, within the scope of the appended claims, the invention may be practiced otherwise than as particularly described.

What is claimed is:

1. A prosthesis for use in in vivo surgery having a coating, respectively, of an ionically charged surfactant and an antibiotic compound encapsulated within phospholipid vesicles, wherein said vesicles have a surface charge opposite to that of said surfactant.

2. The prothesis as defined in claim 1 wherein said antibiotic compound is selected from the group consisting of penicillins, and cefoxitins.

3. The prosthesis as defined in claim 1 wherein said surfactant is tridodecylmethyl ammonium chloride.

4. The prosthesis as defined in claim 3 wherein said vesicles are prepared from phosphatidyl serine.

5. The prosthesis as defined in claim 1 wherein said prosthesis is a vascular graft.

6. A method for preparing a prosthesis for use in in vivo surgery, which comprises:
   (a) contacting said prosthesis with an ionically charged surfactant to coat said prosthesis with said ionically charged surfactant;
   (b) contacting said prosthesis of step (a) with a phospholipid vesicle suspension; and
   (c) removing non-adhering vesicles from the prosthesis of step (b).

7. The method as defined in claim 6 wherein step (a) is effected for a period of time of from 5 to 120 minutes.

8. The method as defined in claim 6 wherein step (a) is effected for a period of 30 minutes.

9. The method as defined in claim 6 wherein step (a) is effected at a temperature of from 0 degrees to 55 degrees C.

10. The method as defined in claim 9 wherein step (a) is effected preferably at ambient temperature.

11. The method as defined in claim 6 wherein step (b) is effected for 16 hours at room temperature.

12. The method as defined in claim 6 wherein the phospholipid vesicle suspension is prepared by sonicating phospholipids suspended in an aqueous solution of a drug.

13. The method as defined in claim 12 wherein a phosphlipid with a net positive charge is employed if the prosthesis has been coated with negatively charged surfactant.

14. The method as defined in claim 12 wherein a phospholipid with a net negative charge is employed if the prosthesis has been coated with a positively charged surfactant.

15. The method as defined in claim 12 wherein the suspension is sonicated with a probe-type sonicator at 5 watts to 50 watts.

16. The method as defined in claim 15 wherein the suspension is sonicated preferably at 20 watts of energy.

17. The method as defined in claim 12 wherein the suspension is sonicated for 60 minutes.

18. The method as defined in claim 17 wherein the suspension is sonicated at a temperature of 25 degrees C.

19. The method as defined in claim 6 wherein said cationic surfactant is tridodecylmethyl ammonium chloride.

20. The method as defined in claim 6 wherein said antibiotic compound is selected from the group consisting of penicillins and cephalosporins.

* * * * *